United States Patent [19]

Schaafsma et al.

[11] 4,016,175
[45] Apr. 5, 1977

[54] PREPARATION OF A 2-AMINO-PYRROLINE DERIVATIVE

[75] Inventors: Sijbrandus E. Schaafsma, Beek(L); Leonardus H. Geurts, Sittard, both of Netherlands

[73] Assignee: Stamicarbon B.V., Geleen, Netherlands

[22] Filed: Sept. 23, 1975

[21] Appl. No.: 616,012

[30] Foreign Application Priority Data

Sept. 26, 1974 Netherlands ............... 7412695

[52] U.S. Cl. ................ 260/326.62; 260/326.9
[51] Int. Cl.$^2$ ............................ C07D 207/22
[58] Field of Search ................... 260/326.62

[56] References Cited

UNITED STATES PATENTS 2,513,270  7/1950  Blecki ................... 260/293.75
3,560,523  2/1971  Etienne et al. ........... 260/326.62

OTHER PUBLICATIONS

Etienne et al.; Chem. Abstr. vol. 72:55133n (1970).
Etienne et al.; Chem. Abstr., vol. 62:2753d (1965).
Etienne et al.; Chem. Abst., vol. 62:9109f (1965).

*Primary Examiner*—Richard J. Gallagher
*Assistant Examiner*—Mary C. Vaughn
*Attorney, Agent, or Firm*—Cushman, Darby & Cushman

[57] ABSTRACT

The novel compound 2-(N-γ-cyanopropyl)-amino-Δ$^1$-pyrroline is prepared by heating γ-amino-butyronitrile in an inert atmosphere to a temperature up to 250° C. and optionally in the presence of a solvent. The product may be hydrolyzed into pyrrolidone-2 and then polymerized to nylon-4.

9 Claims, No Drawings

PREPARATION OF A 2-AMINO-PYRROLINE DERIVATIVE

The present invention relates to a process for the preparation of a new derivative of a 2-amino-pyrroline, which, as used herein, also denotes the tautomeric 2-imino-pyrrolidine.

It is already known, as described in U.S. Pat. No. 2,513,270 and Journal or Organic Chemistry, vol. 32, pg. 738, that heating of a N-substituted amino-butyronitrile in the presence of gaseous hydrogen chloride or hydrogen bromide will produce the correspondingly substituted imino-pyrrolidine.

We have now found that a new derivative of a 2-amino-pyrroline can be obtained by simply heating γ-amino-butyronitrile in the absence of hydrogen chloride and hydrogen bromide, such as by heating for the required period of time in a nitrogen atmosphere.

The process according to the present invention for the preparation of a novel derivative of a 2-amino-pyrroline is characterized in that γ-amino-butyronitrile is subjected to heating to form a 2-amino-pyrroline derivative of the formula:

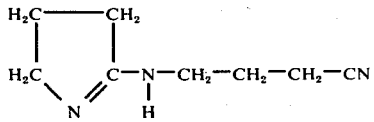

The reaction according to the present invention is conveniently conducted by heating the aminonitrile at various temperatures, such as temperatures up to 250° C. Temperatures of the order of 75°–160° C. are particularly suitable. The pressure at which the reaction is conducted as such is not critical, and hence atmospheric pressure is used by preference although higher and lower pressures may be used. In the process according to the invention ammonia is split off, and 2-amino-$\Delta^1$-pyrroline is formed as a by-product in addition to the novel 2-amino-pyrroline derivative.

The process according to the invention is suitably conducted in the presence of a solvent, such as butanol, toluene, pyrrolidone-2, and pyridine. The choice of the solvent also determines the extent to which said by-product is formed. For example, if butanol is used as the solvent, much more by-product is found to be formed than when use is made of pyridine, pyrrolidone-2 and toluene. The new derivative can easily be separated from the by-product by distillation. The new amino-pyrroline derivative obtained in the process according to the invention is useful and can be hydrolyzed into pyrrolidone-2, a well-known starting material for nylon-4, and so can the by-product formed. In this hydrolysis, 2 moles of pyrrolidone-2 are formed theoretically from 1 mole of the new derivative. The hydrolysis may be according to conventional methods such as those described in the Journal of the Chemical Society 1947, pgs. 1508–1511 and the Journal of Organic Chemistry 1961, pg. 1830, or the Journal of the Chemical Society 1952, pgs. 4268–4271. Preferably the hydrolysis is conducted as described in our concurrently filed copending application Ser. No. 616,011, the disclosure of which is hereby incorporated by reference.

The process according to the invention will be further elucidated and illustrated in the following examples in which all parts and percentages are by weight.

EXAMPLE 1

84 grams (1 mole) of γ-amino-butyronitrile are heated under a nitrogen atmosphere to 100° C. in a flask provided with a stirrer. The reaction mixture was kept at this temperature for 4 hours, after which the development of ammonia that occured during the heating was complete.

The reaction mixture was cooled to room temperature and the liquid was then distilled under reduced pressure. Two fractions were separated off:

Fraction I: 25.2 g of product were obtained at 95°–100° C and 4 mm Hg.

Fraction II: 45.3 g of product were obtained at 113°–120° C and 0.3 mm Hg.

Fraction I solidified upon cooling and was recrystallized from benzene. 21.8 g (yield 26%) of colorless needle-shaped crystals with a melting point of 74.5°–75.5° C were obtained. The following structure was determined by means of mass spectrometry, nuclear spin resonance, and infra-red spectrometry:

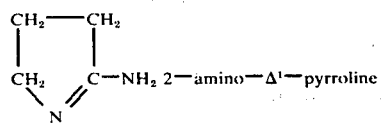

Fraction II was distilled again, when 40.8 g (yield 54%) of product were obtained which solidified upon cooling. The melting point of this product was 30°–32° C. The following structure was determined by means of mass spectrometry, nuclear spin resonance, and infra-red spectrometry:

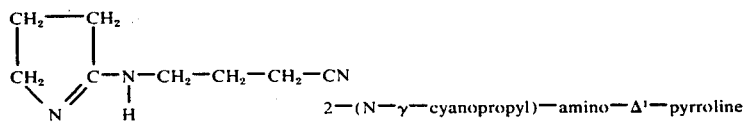

Hydrolysis of the new product into pyrrolidone-2

A mixture of 15.1 g (0.1 mole) of 2-(N-γ-cyanopropyl)-amino-$\Delta^1$-pyrroline and 35 g of water was heated at 210° C in a closed steel tube for 2 hours. Upon cooling to room temperature, the reaction mixture was analyzed gas-chromatographically.

The reaction mixture contained 16.2 g of pyrrolidone-2, which corresponds to a yield of 95.5%.

EXAMPLE 2

γ-amino-butyronitrile (5 g) was dissolved in 45 g of pyridine and heated at 120° C for 20 hours in a flask provided with a stirrer and a reflux cooler under a nitrogen atmosphere. Upon cooling, the resulting reaction mixture was analyzed gas-chromatographically. The reaction mixture consisted of 0.75 g of the starting material γ-amino-butyronitrile, 1.35 g of 2-amino-$\Delta^1$- pyrroline and 2.5 g of 2-(N-γ-cyanopropyl) amino-Δ¹-pyrroline.

Of the converted amount of γ-amino-butyronitrile, 32% was converted into 2-amino-Δ¹-pyrroline and 65% into 2-(N-γ-cyanopropyl)-amino-Δ¹-pyrroline.

EXAMPLE 3

The process of example 2 was repeated, but n-butanol was used as a solvent instead of pyridine. It was found from gas-chromatographic analysis that the reaction mixture contained no γ-amino-butyronitrile. The mixture was found to contain 3.65 g of 2-amino-Δ¹-pyrroline (yield: 73%) and 0.18 g of 2-(N-γ-cyanopropyl)-ΔΔ¹-pyrroline (yield: 4%)

EXAMPLE 4

A mixture of 5 g of γ-amino-butyronitrile in 45 g of toluene as a solvent was heated at 160° C. in a closed steel tube for 6 hours. Upon completion of the reaction and cooling to room temperature, the reaction mixture was analyzed gas-chromatographically. The reaction mixture contained 0.7 g of γ-amino-butyronitrile, 0.95 g of 2-amino-Δ¹-pyrroline, and 1.95 g of 2-(N-γ-cyanopropyl)-aminoΔ¹-pyrroline. 22% of the converted γ-amino-butyronitrile was converted into 2-amino-Δ¹-pyrroline and 50of into 2-(N-γ-cyanopropyl)-amino-Δ¹-pyrroline.

EXAMPLE 5

γ-amino-butyronitrile (8.4 g) was dissolved in 50 g of pyrrolidone-2 and heated at 120° C for 20 hours in a flask provided with a stirrer and a reflux cooler in a nitrogen atmosphere. Upon cooling, the resulting reaction mixture was analyzed gas-chromatographically. The reaction mixture contained 1.93 g of 2-amino-Δ¹-pyrroline and 4.0 g of 2-(N-γ-cyanopropyl)-amino-Δ¹-pyrroline, and no γ-amino-butyronitrile. 23% of the γ-amino-butyronitrile was converted into 2-amino-Δ¹-pyrroline and 53% into 2-(N-γ-cyanopropyl)-aminoΔ¹-pyrroline.

What is claimed is:
1. A process for the preparation of a 2-amino-pyrroline compound, comprising the step of heating γ-amino-butyronitrile at a temperature of 75°–250° C. in an inert atmosphere to form a 2-amino-pyrroline compound of the formula:

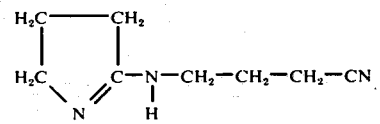

2. The process according to claim 1 wherein the heating is effected at a temperature of 75°–160° C.
3. The process according to claim 1 wherein the reaction is conducted in the presence of a solvent selected from the class consisting of butanol, toluene, pyrrolidone-2 and pyridine.
4. The process according to claim 3 wherein the solvent is pyridine, pyrrolidone-2 or toluene.
5. The process according to claim 1 wherein the process is conducted at atmospheric pressure.
6. A compound of the formula:

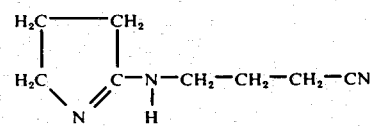

7. The process according to claim 1 wherein the heating is conducted in the absence of a solvent.
8. The process according to claim 1 wherein the heating is effected at a temperature of 100°–160° C.
9. The process according to claim 7 wherein the heating is effected at a temperature of 75°–160° C.